US012758383B2

(12) United States Patent
De Bonis et al.

(10) Patent No.: US 12,758,383 B2
(45) Date of Patent: Oct. 13, 2026

(54) ARTICULATED PROSTHESIS FOR A TRICUSPID OR MITRAL VALVE

(71) Applicant: STAR TRIC S.R.L., Milan (IT)

(72) Inventors: Michele De Bonis, Cernusco Sul Naviglio (IT); Ottavio Alfieri, Brescia (IT); Elisabetta Lapenna, Cernusco Sul Naviglio (IT); Daniele Zanotti, Comelico Superiore (IT); Marco Gard, Borgomasino (IT); Eugenio Maria Passanante, Milan (IT)

(73) Assignee: STAR TRIC S.R.L., Milan (IT)

( * ) Notice: Subject to any disclaimer, the term of this patent is extended or adjusted under 35 U.S.C. 154(b) by 749 days.

(21) Appl. No.: 18/250,680

(22) PCT Filed: Aug. 6, 2021

(86) PCT No.: PCT/IB2021/057257
§ 371 (c)(1),
(2) Date: Apr. 26, 2023

(87) PCT Pub. No.: WO2022/090818
PCT Pub. Date: May 5, 2022

(65) Prior Publication Data
US 2023/0397989 A1 Dec. 14, 2023

(30) Foreign Application Priority Data
Oct. 30, 2020 (IT) ........................ 102020000025879

(51) Int. Cl.
*A61F 2/24* (2006.01)

(52) U.S. Cl.
CPC ............ *A61F 2/2454* (2013.01); *A61F 2/246* (2013.01); *A61F 2220/0016* (2013.01)

(58) Field of Classification Search
CPC ................................ A61F 2/246; A61F 2/2454
See application file for complete search history.

(56) References Cited

U.S. PATENT DOCUMENTS

| | | | | |
|---|---|---|---|---|
| 2010/0022823 | A1 * | 1/2010 | Goldfarb ............ | A61B 17/0401 600/37 |
| 2019/0008643 | A1 | 1/2019 | Delgado et al. | |
| 2019/0209293 | A1 * | 7/2019 | Metchik .................. | A61F 2/246 |
| 2019/0350702 | A1 | 11/2019 | Hernandez et al. | |
| 2020/0163757 | A1 * | 5/2020 | De Bonis ............. | A61B 17/122 |

OTHER PUBLICATIONS

International Search Report and Written Opinion for Corresponding International Application No. PCT/IB2021/057257, 9 pages, Sep. 10, 2021.

* cited by examiner

*Primary Examiner* — Suba Ganesan
(74) *Attorney, Agent, or Firm* — Lucas & Mercanti, LLP

(57) ABSTRACT

An articulated prosthesis, left in the patient's heart for repairing a tricuspid or mitral valve, is disclosed. The prosthesis is designed to grip simultaneously all the three leaflets of the tricuspid valve, or two of the mitral valves, so as to make them lay distended fully in the valve plane and assume a final configuration as in the common surgical procedure, with the leaflets pulled towards the center of the valve.

6 Claims, 10 Drawing Sheets

ARTICULATED PROSTHESIS FOR A TRICUSPID OR MITRAL VALVE

CROSS-REFERENCE TO RELATED APPLICATIONS

This application is a 371 of PCT/IB2021/057257, filed Aug. 6, 2021, which claims the benefit of Italian Patent Application No. 102020000025879, filed Oct. 30, 2020.

TECHNICAL FIELD

This disclosure relates to the repair of heart valves exhibiting valve regurgitation. More particularly, the invention relates to an apparatus suitable for a less invasive repair of a heart valve using an articulated prosthesis deliverable through a catheter, for leaflets of a tricuspid or mitral heart valve.

BACKGROUND

The most common type of tricuspid valve disease is functional tricuspid regurgitation (TR), which is mainly due to the dilatation of the tricuspid annulus secondary to right ventricular enlargement. Later in the course of the disease, tethering of the tricuspid leaflets may also occur because of the displacement of the papillary muscles inside the right ventricle. When functional TR is due to both severe annular dilatation and leaflet tethering, annuloplasty alone is unlikely to be successful. Similarly, TR caused by prolapse or flail of multiple leaflets, as typically seen in post-traumatic and severe degenerative TR, cannot be rectified by a simple annuloplasty procedure.

In order to achieve an effective and durable repair, the so-called 'clover technique' has been proposed. This technique consists in suturing together the central part of the free edges of the tricuspid leaflets, producing a 'clover'-shaped valve. A pictorial representation of a tricuspid valve treated according to this technique is depicted in FIG. 1. Clinical results obtained with this technique are reported in:

"*The 'clover technique' as a novel approach for correction of post-traumatic tricuspid regurgitation*", O. Alfieri, M. De Bonis et al., Journal of Thoracic and Cardiovascular Surgery, 2003; Vol. 126, No. 1, pages 75-79;

"*A novel technique for correction of severe tricuspid valve regurgitation due to complex lesions*." De Bonis M, Lapenna E et al. Eur. J. Cardiothorac. Surg. 2004 May; 25(5):760-5.

"*Four-leaflet clover repair of severe tricuspid valve regurgitation due to complex lesions*", E. Lapenna, M. De Bonis et al., Journal of Cardiovascular Medicine, 2008, Vo. 9 No. 8, pages 847-849;

"*The clover technique for the treatment of complex tricuspid valve insufficiency: midterm clinical and echocardiographic results in* 66 *patients*", E. Lapenna, M. De Bonis et al., European Journal of Cardio-thoracic Surgery, 37 (2010), 1297-1303;

"*Long-term results* (*up to* 14 *years*) *of the clover technique for the treatment of complex tricuspid valve regurgitation*", De Bonis M, Lapenna E, et al. Eur. J. Cardiothorac. Surg. 2017 Feb. 23. doi: 10.1093/ejcts/ezx027.

Devices for catching valve leaflets of a mitral valve as well as of a tricuspid valve, are marketed with the commercial names MITRACLIP™ and TRICLIP™. This prior device, that can be introduced into the heart through a catheter by a vascular approach or throughout a small incision in the chest, comprises a fastener applicator of the type shown in FIG. 2. The sequence of operations to be performed for implanting a MITRACLIP™ fastener is shown in FIG. 3. In the depicted case the heart valve is the mitral valve, though the same observations hold mutatis mutandis also for the tricuspid valve. Using a catheter, the MITRACLIP™ fastener is inserted in a folded configuration into the heart; when the catheter is close to the heart valve, the fastener is deployed like an umbrella to catch the leaflets of the valve, and it is subsequently closed to grip the leaflets together. Finally, the MITRACLIP™ fastener is left closed in the heart for keeping the leaflets together, thus reducing valve regurgitation.

Unfortunately, tests carried out by the applicant have shown that this prior applicator with two arms is unable to catch simultaneously all the 3 leaflets of the tricuspid valve and, therefore, its efficacy in treating tricuspid regurgitation is very limited. In presence of very dilated tricuspid annulus, catching also of just 2 leaflets of the tricuspid valve is rather difficult with the MitraClip™ system. When more MitraClips™ are implanted in the aim of improving the competence of the tricuspid valve, the risk of tricuspid stenosis significantly increases by reducing too much the orifice of the repaired tricuspid valve. Without being bound to a theory, the increased risk of stenosis may be due to the fact that the central portions of the leaflets of the heart valve are folded at a right angle in respect to the plane of the heart valve in order to be gripped together one against the other. The leaflets assume an unnatural configuration overstretched toward the center of the valve plane, thus the light therebetween is reduced and the risk of stenosis is increased.

A relevant improvement in respect to the MITRACLIP fastener is represented by the articulated prosthesis of FIGS. 4 to 6B, which is conceived so as to grip simultaneously all the three leaflets of a tricuspid valve so as to make them lay distended fully in the valve plane and to assume a final configuration as in the common surgical procedure.

The articulated prosthesis 5 in a distended configuration is illustrated in FIG. 4. It comprises:

- a distal annular cylindrical portion 6,
- a central annular cylindrical portion 7,
- a proximal annular cylindrical portion having a cylindrical collar 8 and a screw 9 engaged into the collar 8 and supported thereby so as to be free to rotate along a longitudinal axis,
- a first plurality of arms 10 hinged to an outer side surface of the distal annular cylindrical portion 6,
- a second plurality of arms 11 hinged to an outer side surface of the collar 8,
- a third plurality of arms 12 each of which is hinged to an outer side surface of the central annular cylindrical portion 7, from one end, and to a corresponding end of a arm from the opposite end,
- a fourth plurality of arms 13 each of which is hinged to an outer side surface of the central annular cylindrical portion 7, from one end, and to a corresponding end of a arm 11 from the opposite end.

The distal portion 6 has an internal screw thread 14 configured to engage with the screw 9 when the articulated prosthesis 5 passes from the distended configuration of FIG. 5 to the expanded configuration of FIGS. 6A and 6B. The central portion 7 has a through hole to let the screw 9 pass therethrough. By screwing the screw 9 in the distal portion 6, the arms 10, 11, 12, 13 are extended and the arms 12 and 13 grab between them the leaflets of the heart valve. When the screw 9 is tightened in the screw thread 14, the articulated prosthesis 5 holds firmly the heart valve leaflets and is left in place as a prosthesis, that may be easily removed by a surgeon if necessary.

The arms shall be configured to catch firmly the leaflets and preventing them from slipping out.

In order to provide a good gripping of the leaflets, at least one of the facing arms 12 and 13 has a knurling 15 and a pointed projection 16 configured to spike the tissue of the corresponding leaflet. In the depicted embodiment only the arms 13 are provided with the knurling 15 and the projection 16, though they may be realized also on some or all of the arms 12 for catching even better the leaflets of the heart valve.

The relative position of the pointed projection 16 on the arm 13 may be established to spike a heart valve leaflet as close as possible to the tip, as shown in FIG. 1 and as it would be done in the classic surgical technique. This result may be attained for example by placing the pointed projections 16 at about the middle of the arm 13.

SUMMARY

Even if this articulated prosthesis provides better results in respect to other similar prosthesis, the way in which the leaflets are caught may still be improved. More in detail, the applicants found that it is possible to realize an articulated prosthesis configured so as to pull the leaflets of a human valve towards the center of the valve, as it would be done with the surgical procedure illustrated in FIG. 1.

This outstanding result is attained with an articulated prosthesis as defined in the enclosed claim 1.

Further embodiments are defined in the enclosed claims.

DETAILED DESCRIPTION OF EXEMPLARY EMBODIMENTS

In the ensuing description reference will be made to the repair of a tricuspid valve, though the same observations hold mutatis mutandis for the repair of a mitral valve. For this reason, the articulated prosthesis shown in the figures has three rows of arms regularly disposed around circular side surfaces of the catching device in order to grip the three leaflets of a tricuspid valve. Nevertheless, the depicted prosthesis 5 could be made with only two rows of arms for gripping the two leaflets of a mitral valve, or even with four or more rows of arms for better catching the leaflets of any heart valve.

Figure 7A:
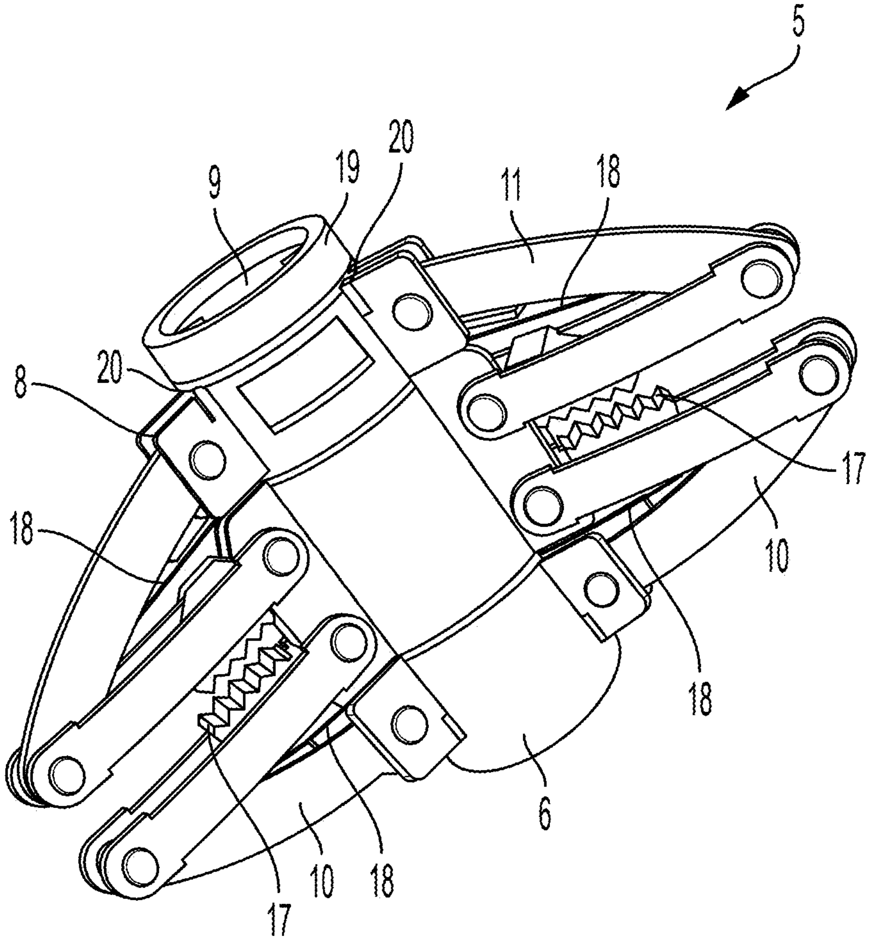
FIGS. 7A to 7C depict the articulated prosthesis of this disclosure in an extended configuration with the screw of the proximal portion tightly screwed into the distal portion.
Figure 7B:
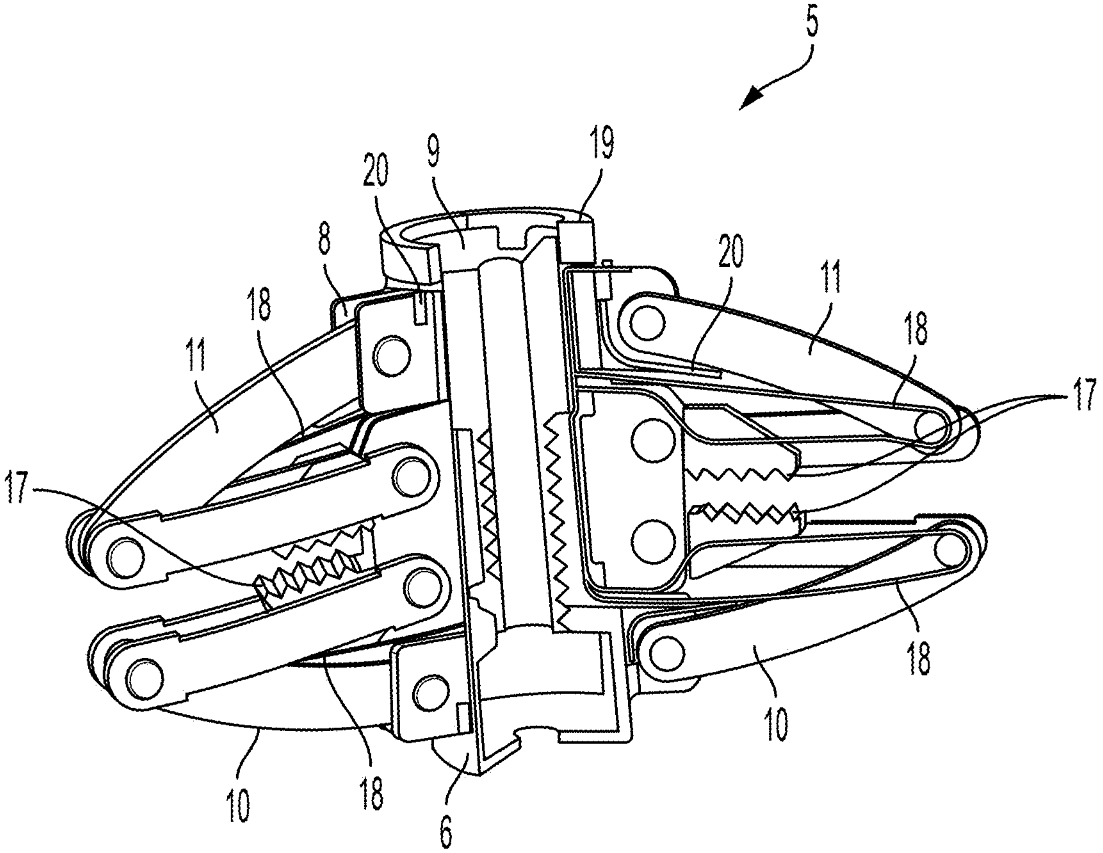
Figure 7C:
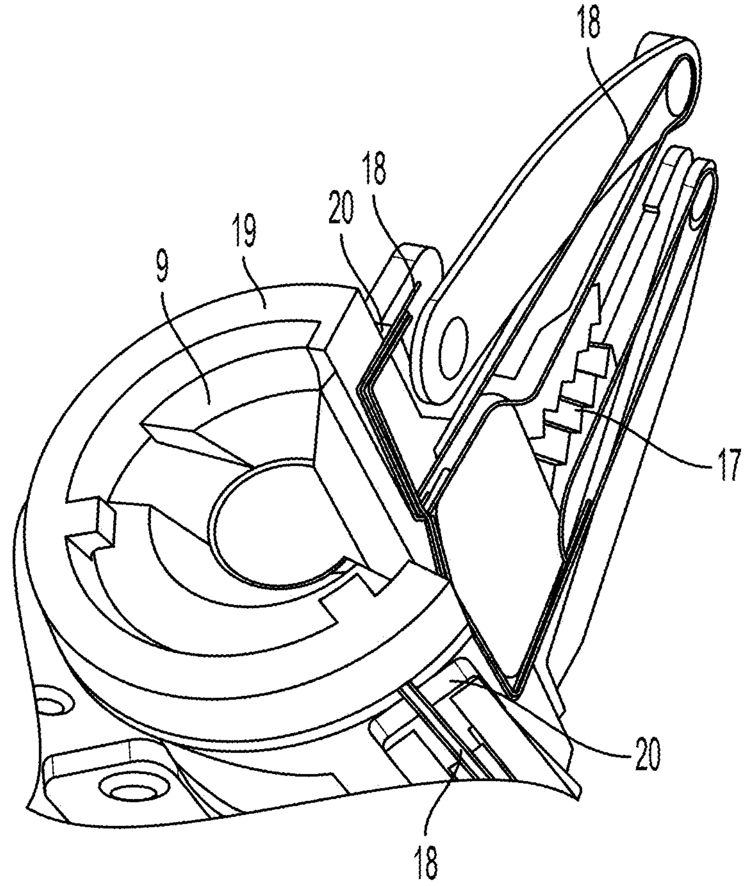

The articulated prosthesis of this disclosure is depicted in FIGS. 7A to 7C, wherein the same components bear the same reference numbers. As the prior prosthesis of FIGS. 4 to 6B, the articulated prosthesis of this disclosure has a distal annular portion, a central annular portion and a proximal annular portion; a first plurality of arms hinged to an outer side surface of the distal annular portion; a second plurality of arms hinged to an outer side surface of the proximal annular portion; a third plurality of arms each of which is hinged to an outer side surface of the central annular portion, from one end, and to a corresponding end of a arm of the first plurality, from an opposite end; and a fourth plurality of arms each of which is hinged to an outer side surface of the central annular portion, from one end, and to a corresponding end of a arm of the second plurality, from an opposite end.

As in the prior prosthesis, the distal annular portion has an internal screw thread, the central annular portion defines a through hole for letting the proximal annular portion pass through, and the proximal annular portion has:

- a cylindrical collar on a side surface of which the second plurality of arms is hinged, and
- a screw engaged into the collar and supported thereby so as to be free to rotate along a longitudinal axis of the screw, the screw being configured to engage with the internal screw thread.

The articulated prosthesis is movable from a distended configuration (not shown in the figures), in which all the arms hinged in correspondence of their ends are distended, to an expanded configuration, in which the proximal annular portion is threaded throughout the central annular portion and is engaged with the distal annular portion, the arms of the third plurality and fourth plurality being configured to hold therebetween leaflets of a tricuspid or mitral valve.

Differently from the prior prosthesis, the arms of the third plurality and/or of the fourth plurality are equipped with sliders 17. Each slider 17 is configured to be suspended between a respective pair of arms to slide back and forth in a radial direction of the articulated prosthesis when the prosthesis is in the expanded configuration. The sliders 17 have a catching surface configured to grasp by friction leaflets of a tricuspid or mitral valve, and have at least one respective wire 18 fixed thereto and configured to pull the slider 17 radially outwards, when the wire 18 is pulled in a first direction, and to pull the slider 17 radially inwards, when the wire 18 is pulled in the opposite direction.

According to one aspect, each slider 17 has a surface with teeth configured to grasp a leaflet of a tricuspid or mitral valve by cooperating with a facing slider 17.

According to one aspect, not shown in the drawings, there may be sliders 17 in the form of a plate having a surface with a knurling configured to grasp by friction a leaflet of a tricuspid or mitral valve.

Figure 1:
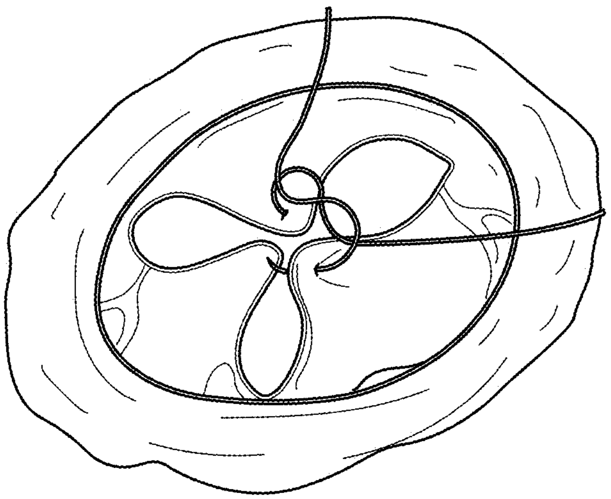
FIG. 1 schematically depicts a typical configuration of a tricuspid valve after the so-called "clover technique" surgical intervention.
Figure 2:
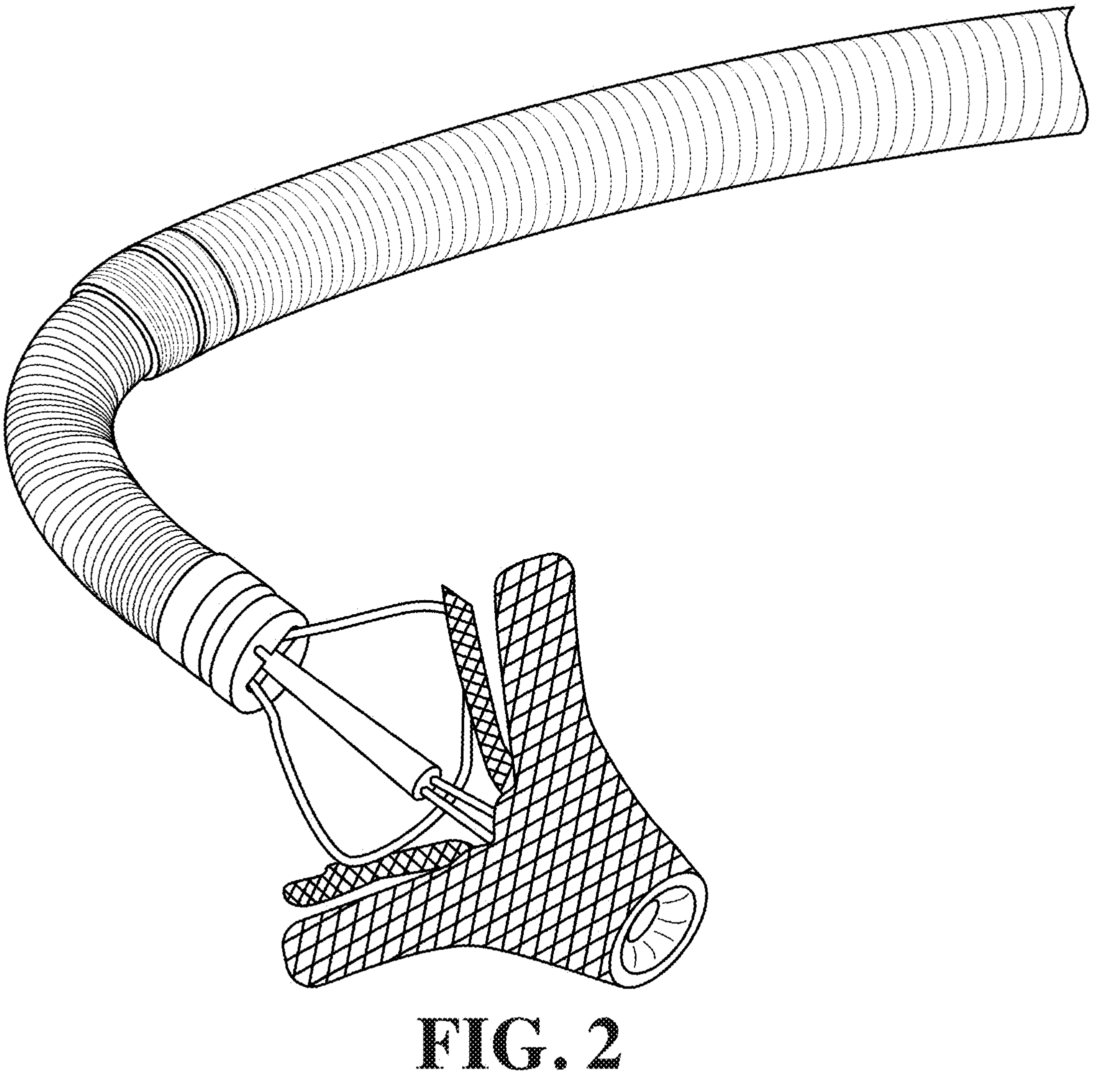
FIG. 2 depicts a prior fastener for leaflets of a mitral or tricuspid valve.
Figure 3:
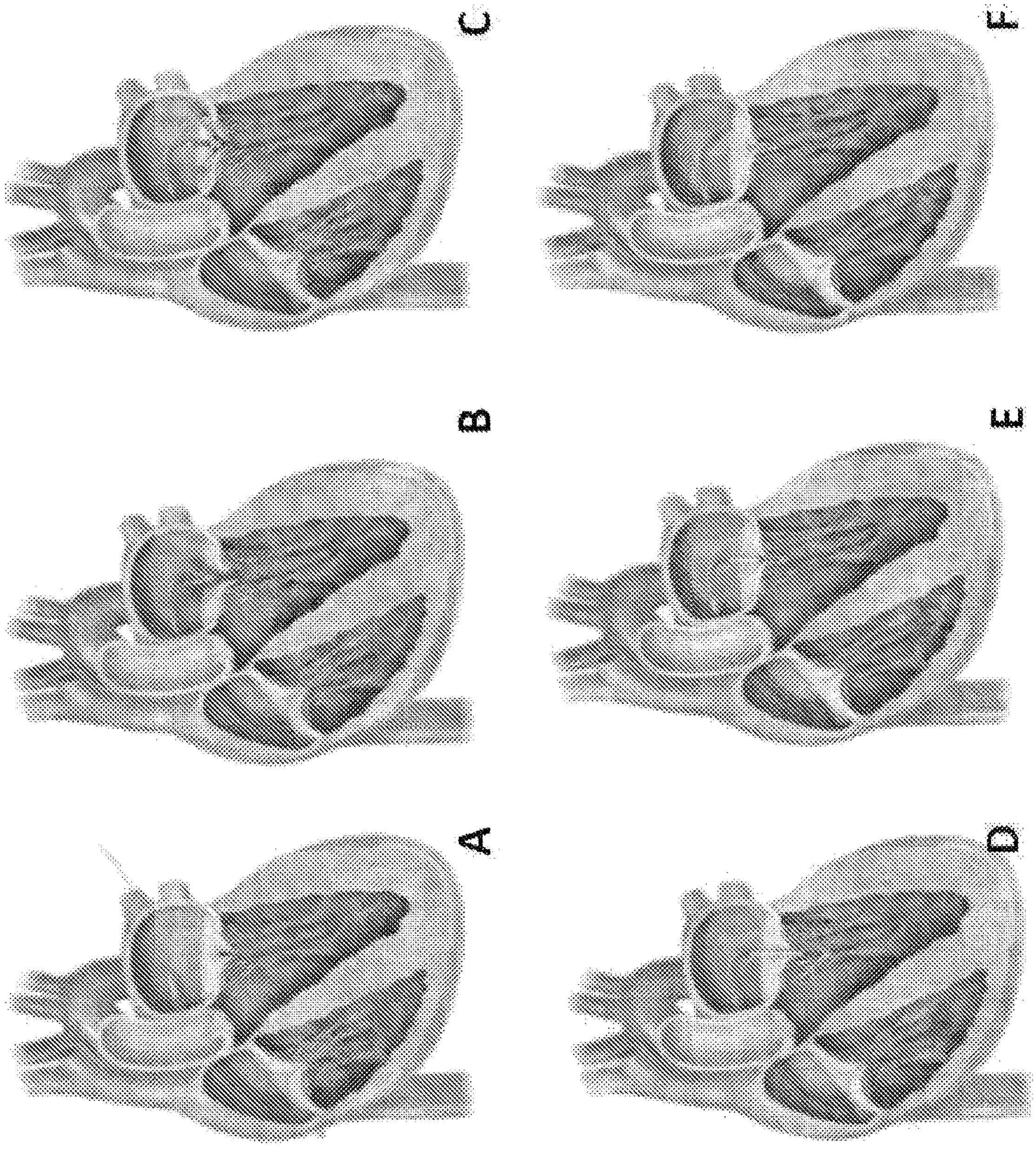
FIG. 3 shows various steps for implanting the so-called MITRACLIP™ fastener to leaflets of a heart valve.
Figure 4:
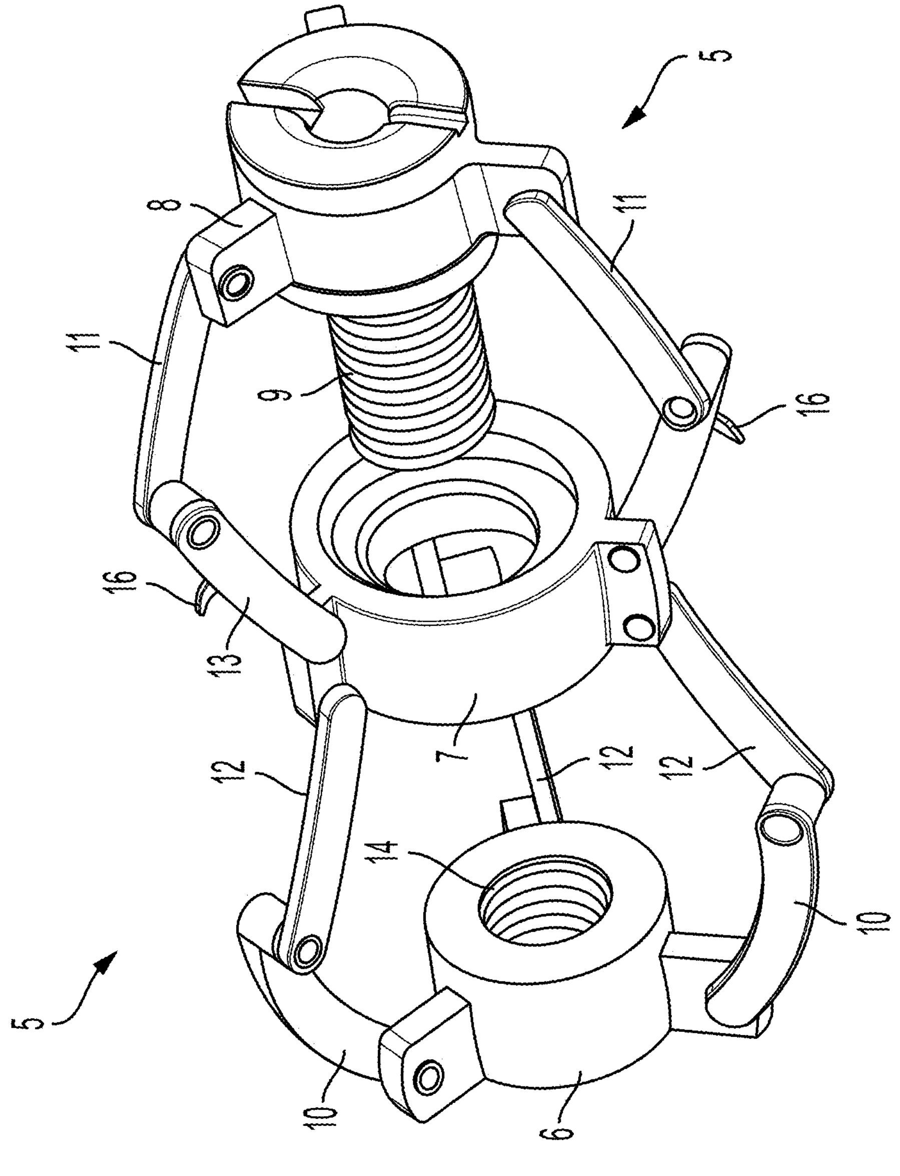
FIG. 4 depicts an articulated prosthesis in a distended configuration.
Figure 5A:
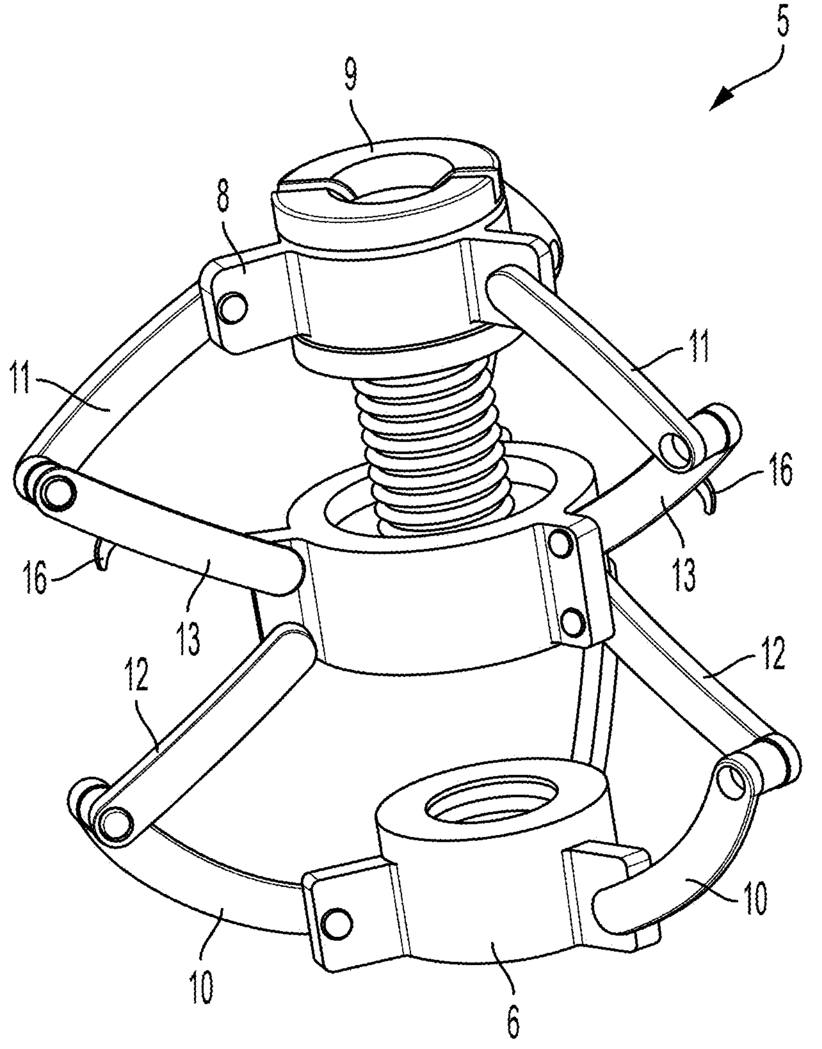
FIGS. 5A and 5B depict the articulated prosthesis of FIG. 4 in a half-extended configuration.
Figure 5B:
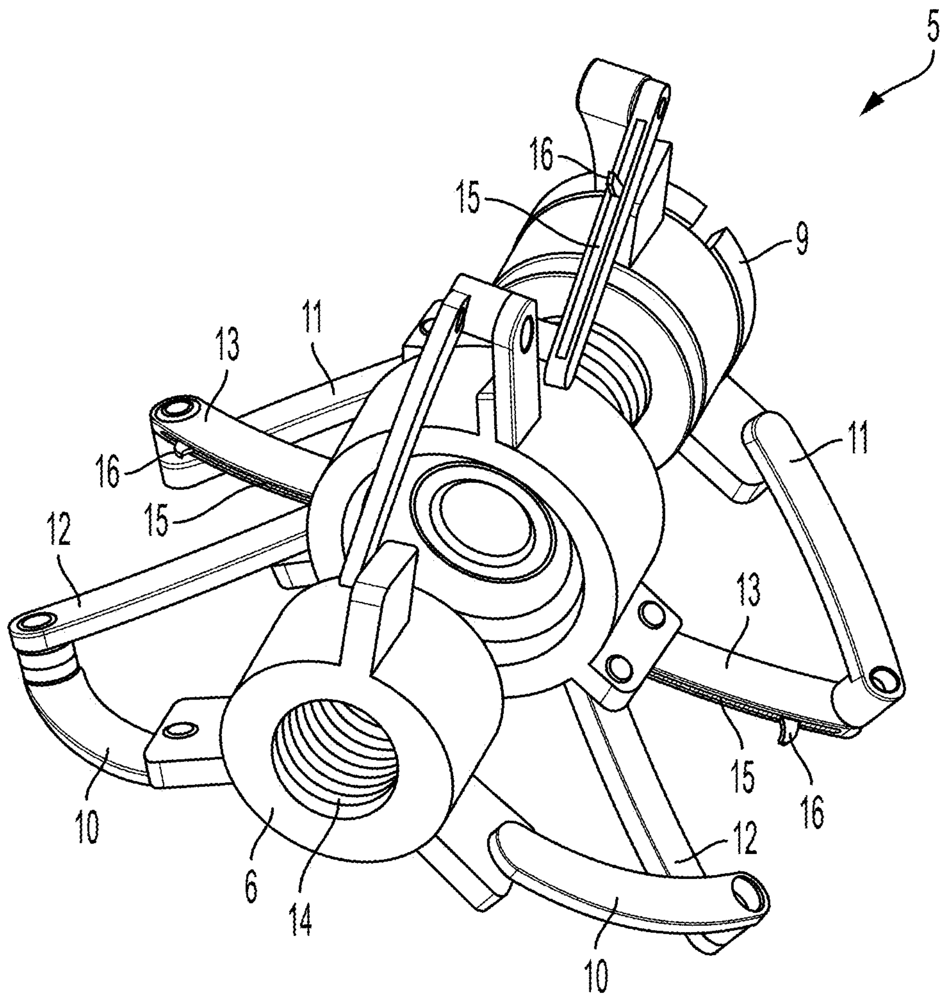
Figure 6A:
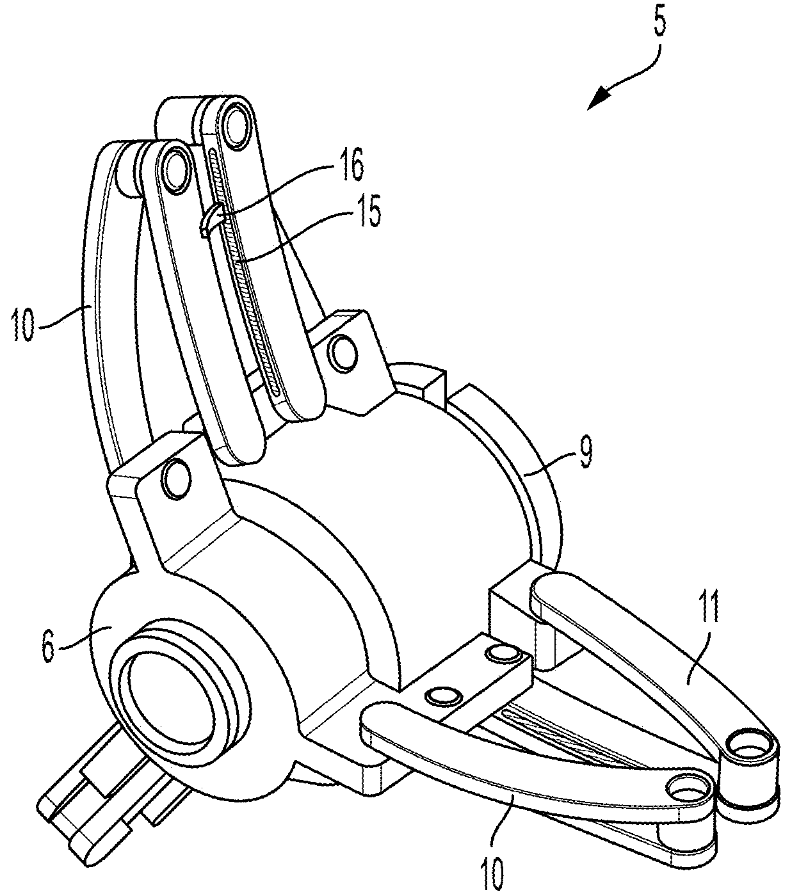
FIGS. 6A and 6B depict the articulated prosthesis of FIG. 4 in an extended configuration with the screw of the proximal portion tightly screwed into the distal portion.
Figure 6B:
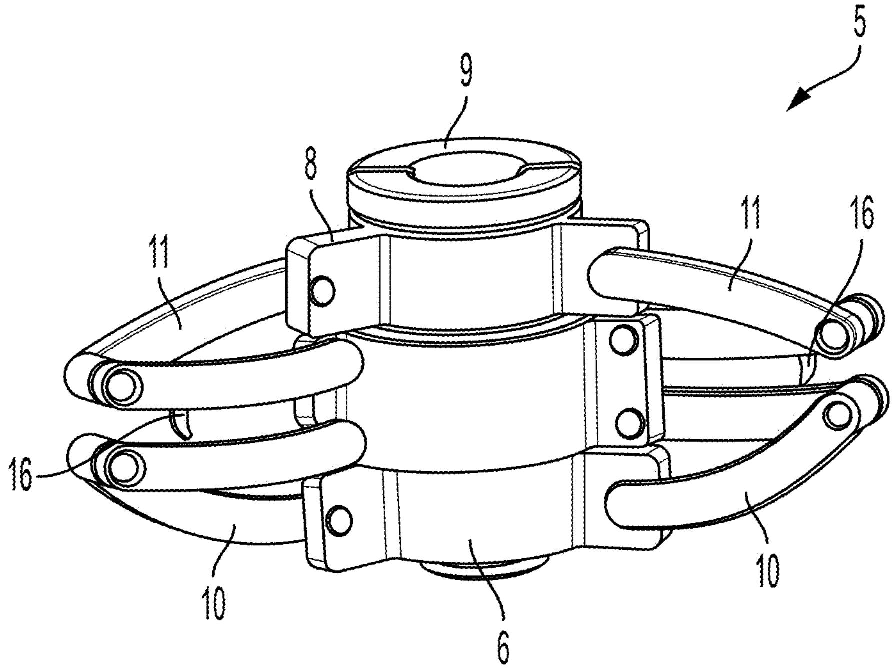

According to one aspect, shown in the figures, the wires 18 enter in the proximal annular portion 8, cross axially the central annular portion 7, run radially outwards and are fixed to a slider 17, turn around an outer pin that hinges an end of one arm of the second plurality of arms to at least one arm of the fourth plurality of arms, run radially towards the center, cross axially the central annular portion 7 and then exit from the proximal annular portion 8. Once the leaflets of a valve are caught between the teeth of facing sliders 17, the wires 18 are pulled so as the leaflets are dragged towards the center of the valve as in the common surgical procedure. When the leaflets are distended, the wires 18 are blocked using a holding mechanism 20 so as the leaflets are kept distended and pulled as they were sewn together (as show in FIG. 1).

According to one aspect, illustrated in the detail view of FIG. 7C, the holding mechanism comprises an element 20 fixed to the cylindrical collar 8. The element has a slit and is positioned so as to intercept a path along which at least one wire 18 is disposed. When the leaflets are caught between two facing sliders 17, the wires 18 are pulled so as to drag the leaflets towards the center of the valve, the wires 18 are forcibly inserted in the slit of the element 20 and are kept pulled. Finally, the wires 18 are cut by a surgeon so as its terminations are held firmly in the slit of the element 20.

According to one aspect, the holding mechanism is equipped with a ring 20 mounted around the head of the screw 9 and configured so as, when the screw 9 is tightened, the ring 20 is held against the cylindrical collar 8 and cooperates to it to sandwich the terminations of the wires 18.

According to one aspect, the number of arms of the second plurality and third plurality is twice the number of arms of the first plurality and fourth plurality, wherein each arm of the fourth plurality is hinged together with two arms of the second plurality, and each arm of the third plurality is hinged together with two arms of the first plurality.

The invention claimed is:

1. An articulated prosthesis for a tricuspid or a mitral valve, comprising:

a distal annular portion, a central annular portion and a proximal annular portion;

a first plurality of arms hinged to an outer side surface of said distal annular portion;

a second plurality of arms hinged to an outer side surface of said proximal annular portion;

a third plurality of arms each of which is hinged to an outer side surface of said central annular portion, from one end, and to a corresponding end of an arm of said first plurality, from an opposite end;

a fourth plurality of arms each of which is hinged to an outer side surface of said central annular portion, from one end, and to a corresponding end of an arm of said second plurality, from an opposite end;

said distal annular portion having an internal screw thread, said proximal annular portion having:

a cylindrical collar on a side surface of which said second plurality of arms is hinged, and a screw engaged into said collar and supported thereby so as to be free to rotate along a longitudinal axis of the screw, the screw being configured to engage with said internal screw thread, said central annular portion defining a through hole for letting said screw pass through;

the articulated prosthesis being movable from a distended configuration, in which all said arms hinged in correspondence of their ends are distended, to an expanded configuration, in which said screw is threaded throughout said central annular portion and is engaged with said distal annular portion, the arms of said third plurality and fourth plurality being configured to hold therebetween leaflets of a tricuspid or mitral valve, wherein said arms of said third plurality and/or of said fourth plurality are equipped with sliders, each slider of said sliders being configured to be suspended between a respective pair of said arms of said third plurality and/or of said fourth plurality and to slide back and forth along said respective pair of arms in a radial direction of said articulated prosthesis when the prosthesis is in said expanded configuration;

each slider of said sliders has a catching surface configured to grasp by friction leaflets of a tricuspid or mitral valve, and has a respective wire fixed thereto and configured to pull said slider radially outwards, when the wire is pulled in a first direction, and to pull said slider radially inwards, when the wire is pulled in a second direction opposite to said first direction; and said proximal annular portion being equipped with a holding mechanism configured to hold pulled said wire;

wherein said wire enters in said proximal annular portion, crosses axially said central annular portion in said first direction, runs radially outwards and it is fixed to said slider, turns around an outer pin that hinges an end of an arm of said second plurality of arms to an arm of said fourth plurality of arms, runs radially inwards, crosses axially said central annular portion in said second direction and then exits from said proximal annular portion.

2. The articulated prosthesis of claim 1, wherein said holding mechanism comprises:

an element with a slit fixed to said cylindrical collar, said element with the slit being placed to intercept a path along which said wire is disposed, wherein said wire is held pulled when both its terminations are forcibly inserted in said slit.

3. The articulated prosthesis of claim 1, wherein each slider of said sliders has a surface with teeth configured to grasp a leaflet of a tricuspid or mitral valve.

4. The articulated prosthesis of claim 1, wherein said sliders are in the form of a plate having a surface with a knurling configured to grasp by friction a leaflet of a tricuspid or mitral valve.

5. The articulated prosthesis of claim 1, wherein the number of said arms of said second plurality and third plurality is twice the number of arms of said first plurality and fourth plurality, each arm of said fourth plurality is hinged together with two arms of said second plurality at said opposite end, each arm of said third plurality is hinged together with two arms of said first plurality at said opposite end.

6. The articulated prosthesis of claim 1 for a tricuspid valve, wherein each of said pluralities of arms comprises three arms or an integer multiple of three arms.

* * * * *